United States Patent [19]
Partyka et al.

[11] 3,974,165
[45] Aug. 10, 1976

[54] HYPOTENSIVE AGENTS

[75] Inventors: Richard Anthony Partyka; Henry Michael Holava, both of Liverpool; Warren Neil Beverung, Minoa, all of N.Y.

[73] Assignee: Bristol-Myers Company, New York, N.Y.

[22] Filed: Dec. 23, 1974

[21] Appl. No.: 535,593

Related U.S. Application Data

[63] Continuation-in-part of Ser. No. 441,619, Feb. 21, 1974, abandoned.

[52] U.S. Cl. .................... 260/287 CF; 260/286 R; 260/287 C; 424/258
[51] Int. Cl.² ............... C07D 215/38; C07D 215/58
[58] Field of Search.... 260/288 R, 286 CF, 287 CF, 260/287 C

[56] References Cited
OTHER PUBLICATIONS

Tanaka et al., Jour. Het. Chem., vol. 9 (1972) pp. 1355–1358.

*Primary Examiner*—Paul M. Coughlan, Jr.
*Attorney, Agent, or Firm*—Robert E. Havranek

[57] ABSTRACT

Optionally substituted 1-H-2,3,3a,4-Tetrahydro-2-oxopyrrolo[2,3-b]quinolines or the pharmaceutically acceptable salts thereof are compounds useful as blood platelet anti-aggregative and/or antihypertensive agents in mammals, including humans.

19 Claims, No Drawings

HYPOTENSIVE AGENTS

CROSS-REFERENCE TO RELATED APPLICATION

This application is a continuation-in-part of a copending application Ser. No. 441,619, filed Feb. 21, 1974, now abandoned.

BACKGROUND OF THE INVENTION

1. Field of the Invention

The compounds of the present invention are useful in the control of mild to severe hypertension and as anticlotting agents.

2. Description of the Prior Art:

The compounds of the present invention are new and novel. The literature discloses the following prior art:

A. A particularly pertinent piece of prior art is the article of Jen et al, J. Med. Chem. 16, 633 (1973), which article describes the compounds having the formulas

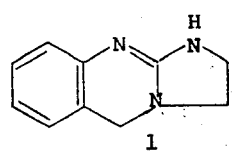
1

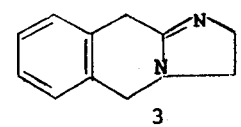
2

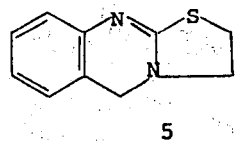
3    4 and

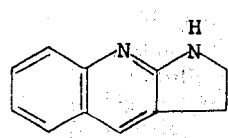
5

The article describes the evaluation of the compounds for their antihypertensive activity and points out the lack of predictability of the antihypertensive activity between the various isosteres. Particular surprise is expressed at the low degree of antihypertensive activity found in compound 2 as compared to compound 1.

B. Another particularly pertinent reference is the article of Tanaka et al, J. Het. Chem., 9, 1355 (1972), which article describes the compounds having the formulas

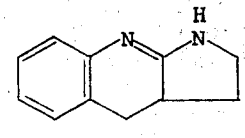
XI

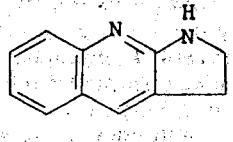
X

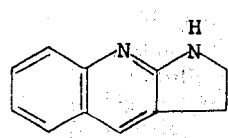
XIV    XIII and

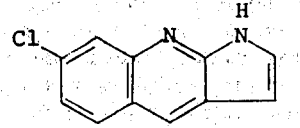
IXb plus other related derivatives. Nothing is reported on the biological activity of the compounds.

With regard to compounds XIII and XIV, Tanaka reports that attempts to prepare them by the Perkin and Robinson method, J. Chem. Soc., 103, 1973 (1913), did not produce XIII and XIV but rather produced XIII$^1$ and XIV$^1$ which respectively are

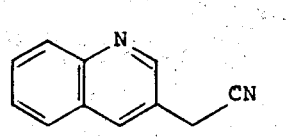
XIII' and

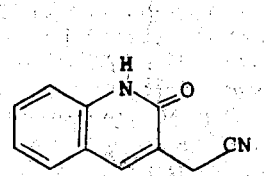
XIV'

C. Other references relating to the basic nucleus, e.g.,

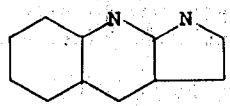

are found in (1) Chem. Abst. 7, 2229 (1913); (2) Chem. Abst. 7, 909 (1914); (3) Chem. Abst. 53, 11416d; (4) Chem. Abst. 70, 77902y (1969); (5) Chem. Abst. 71, 81325a (1969); (6) Chem. Abst. 71, 124290e (1969); (7) Chem. Abst. 72, 126206 (1970); (8) Chem. Abst. 72, 66917x (1970); and (9) Chem. Abst. 75, 20379g (1971).

SUMMARY OF THE INVENTION

The compounds having the formula

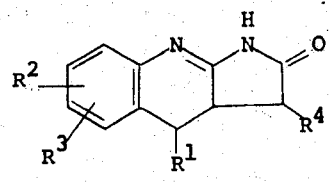
I in which R[1] and R[4] are alike or different and each is H, phenyl or (lower)alkyl, R[2] and R[3] when different are hydrogen, chloro, bromo, fluoro, SO$_3$H, CF$_3$, hydroxy, nitro, amino, phenyl, (lower)alkyl or (lower)alkoxy, R[2] and R[3] when alike are hydrogen, chloro, bromo, fluoro, hydroxy, (lower)alkoxy of 1 to 3 carbon atoms, or (lower)alkyl of 1 to 3 carbon atoms, or when taken together R[2] and R[3] are methylenedioxy or the residue of a phenyl ring; or a pharmaceutically acceptable acid addition salt thereof are hypotensive and/or blood platelet antiaggregative agents.

DETAILED DESCRIPTION

This invention relates to new synthetic compounds of value as hypotensive and blood platelet antiaggregative agents. Most particularly the compounds of the invention are 1-H-2,3,3a, 4-tetrahydro-2-oxopyrollo[2,3-b]quinolines having the formula

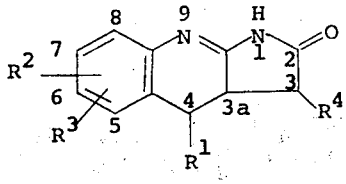

in which R[1] and R[4] are alike or different and each is H, phenyl or (lower)alkyl, R[2] and R[3] when different are hydrogen, chloro, bromo, fluoro, CF$_3$, SO$_3$H, hydroxy, nitro, amino, phenyl, (lower)alkyl or (lower)alkoxy of 1 to 3 carbon atoms, R[2] and R[3] when alike are hydrogen, chloro, bromo, fluoro, hydroxy, (lower)alkyl or (lower)alkoxy of 1 to 3 carbon atoms, or when taken together R[2] and R[3] are methylenedioxy or the residue of a phenyl ring; or a pharmaceutically acceptable acid addition salt thereof.

Hypertension is a rather common and serious disease, particularly in elderly people. High blood pressure, a result of hypertension, is a common but serious disease. Most particularly, hypertension is often the cause of crippling of fatal strokes in the elderly. It was therefore an object of the present invention to provide compounds useful in the treatment of mild to severe hypertension.

Subsequent to the preparation of some of the compounds of the present invention, it was found that most of the compounds also possessed unique properties as blood platelet anti-aggregative agents. These compounds are useful in the prevention of intravascular thromboses, prevention of coronary thrombosis, prevention of transient ischemic episodes, prevention of platelet thrombosis in the use of prosthetic devices (artificial heart valves, etc.).

The objects of the present invention have been achieved by the provision of the compound having the formula

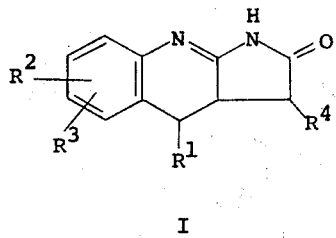

I in which R[1], R[2], R[3], and R[4] are defined above.

For the purpose of this disclosure, the compounds of the present invention are represented as having the formula I. However, compound I can exist in several possible tautomeric forms. e.g.:

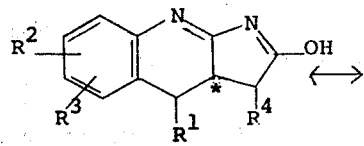

Ia

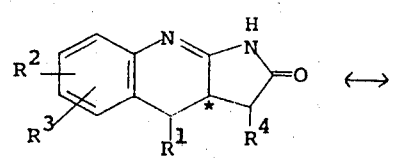

I

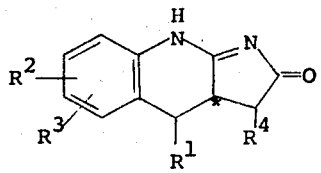

Ib

All the possible tautomers are considered an integral part of the present invention and all these forms are considered included when the compounds are represented as formula I.

Compound I has an asymmetric carbon atom at C-3a as indicated by the asterisk. As such, the compounds exist as (+) and (−) isomers. Accordingly, the scope of the invention is meant to include all the unresolved mixtures and the essentially pure (+) and (−) isomers of the compounds of formula I.

The compounds can be resolved by those methods commonly employed in the art, for example by the use of an optically pure acid such as (+) or (−) camphorsulfonic acid, (+) or (−) tartaric acid, etc.

The nontoxic salts that are pharmaceutically acceptable include the hydrochlorides, hydrobromides, hydroiodides, (lower)alkylsulfates, (lower)alkyl and aryl sulfonates, phosphates, sulfates, maleates, fumarates, succinates, tartrates, citrates, and other commonly used in the art.

The salts obtained through the variation of the acid used in some cases have special advantage due to increased stability, increased solubility, decreased solubility, ease of crystallization, lack of objectionable taste, etc., but these are all subsidiary to the main physiological action of the free base, which is independent of the character of the acid used in the preparation of the salt.

Most of the compounds of the present invention can be prepared as shown in Chart I.

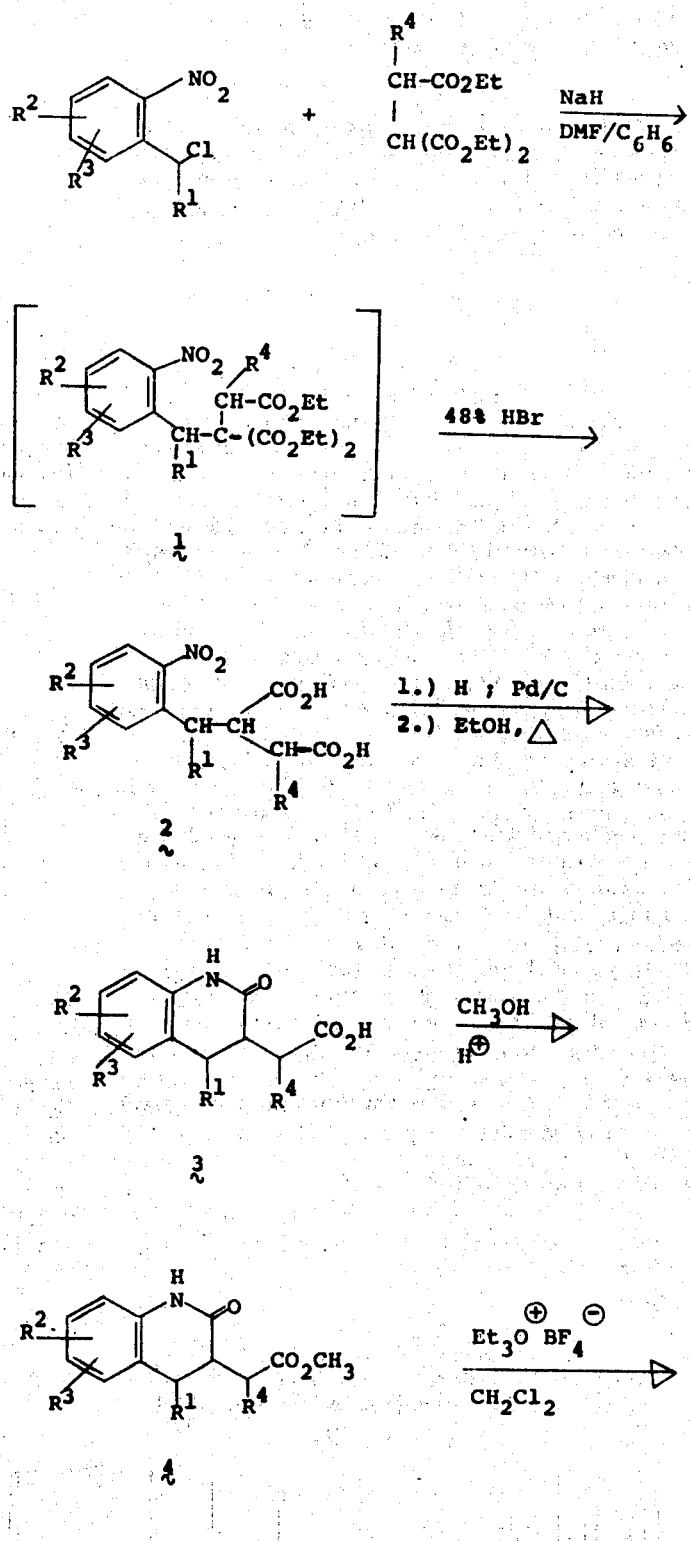

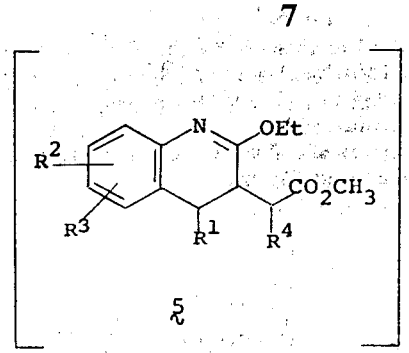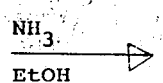

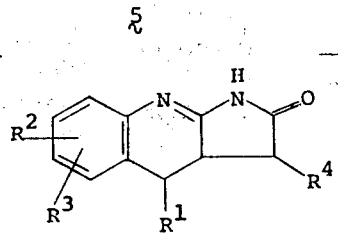

in which $R^1$, $R^2$, $R^3$ and $R^4$ are as described above.

In other cases, particularly when $R^2$ or $R^3$ is a chlorine, bromine or $NO_2$, it may be desirable to chlorinate, brominate or nitrate after producing the unsubstituted compound I (see examples 15, 16 and 17).

The objectives of the present invention have been achieved by the provision according to the present invention, of the process for the synthesis of compounds having the formula

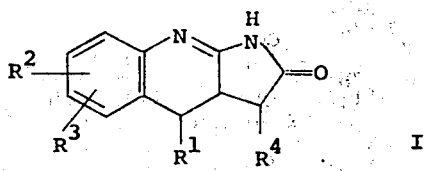

in which $R^1$ and $R^4$ are alike or different and each is H, phenyl or (lower)alkyl, $R^2$ and $R^3$ when different are hydrogen, chloro, bromo, fluoro, $CF_3$, hydroxy, nitro, amino, phenyl, (lower)alkyl or (lower)alkoxy of 1 to 3 carbon atoms, $R^2$ and $R^3$ when alike are hydrogen, chloro, bromo, fluoro, hydroxy, (lower)alkoxy or (lower)alkyl of 1 to 3 carbon atoms, or when taken together $R^2$ and $R^3$ are methylenedioxy or the residue of a phenyl ring; which process comprises the consecutive steps of A. treating the compound having the formula

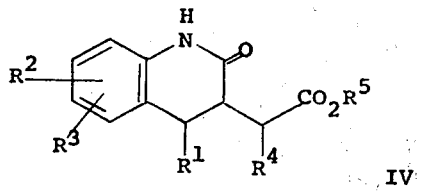

in which $R^5$ is (lower)alkyl and $R^1$, $R^2$, $R^3$ and $R^4$ are as described above, with triethyloxonium tetrafluoroborate to produce the intermediate having the formula

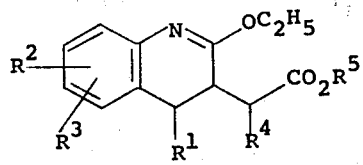

in which $R^1$, $R^2$, $R^3$, $R^4$ and $R^5$ are as described above; and

B. isolating compound V in anhydrous form and treating it with a (lower)alkanol saturated with anhydrous ammonia, to produce the compound having the formula

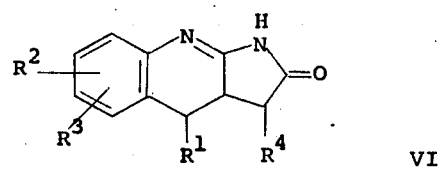

in which $R^1$, $R^2$, $R^3$ and $R^4$ are as defined above.

A more preferred embodiment is the process for the preparation of the compounds having the formula

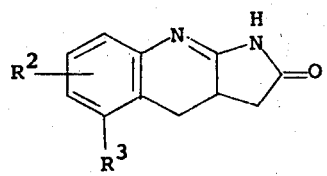

in which $R^2$ and $R^3$ when different are hydrogen, chloro, bromo, fluoro, $CF_3$, hydroxy, nitro, amino, phenyl, (lower)alkyl or (lower)alkoxy of 1 to 3 carbon atoms, $R^2$ and $R^3$ when alike are hydrogen, chloro, bromo, fluoro, hydroxy, (lower)alkyl or (lower)alkoxy of 1 to 3 carbon atoms, or when taken together $R^2$ and $R^3$ are methylenedioxy or the residue of a phenyl ring; which process comprises the consecutive steps of A. treating the compound having the formula

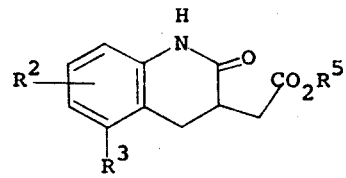

in which $R^5$ is (lower)alkyl and $R^2$ and $R^3$ are as described above, with triethyloxonium tetrafluoroborate in a ratio of at least 1 mole of tetrafluoroborate per mole of compound IV, but preferably about 1.7 moles of tetrafluoroborate per mole of IV, at about room temperature, in a reaction inert solvent preferably methylene chloride, for at least 30 minutes, but preferably 3 hours, to produce the compound having the formula

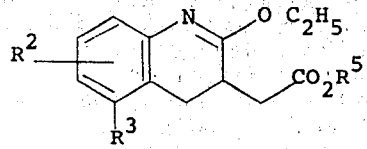

in which $R^5$, $R^2$ and $R^3$ are as described above; and

B. isolating compound V in anhydrous form and treating it with a (lower)alkanol, preferably ethanol, saturated with anhydrous ammonia, initially at room temperature, followed by refluxing for at least one hour, to produce the compound having the formula

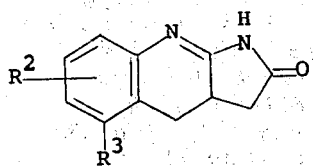

in which $R^2$ and $R^3$ are as defined above.

The pharmaceutically acceptable, nontoxic salts of compound I are readily prepared by the addition of stoichiometric (or larger) quantities of the desired acid to a solution of compound I. Since compound I has only one strongly basic group, it only forms monosalts, e.g., monohydrochloride.

A preferred embodiment of the present invention is the compound having the formula

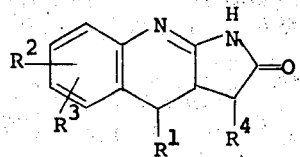

in which $R^1$ and $R^4$ are alike or different and each is H, phenyl or (lower)alkyl, $R^2$ and $R^3$ when different are hydrogen, chloro, bromo, fluoro, $CF_3$, $SO_3H$, hydroxy, nitro, amino, phenyl, (lower)alkyl or (lower)alkoxy of 1 to 3 carbon atoms, $R^2$ and $R^3$ when alike are hydrogen, chloro, bromo, fluoro, hydroxy, (lower)alkyl or (lower)alkoxy of 1 to 3 carbon atoms, or when taken together $R^2$ and $R^3$ are methylenedioxy or the residue of a phenyl ring (—CH=CH—CH=CH—); or a pharmaceutically acceptable acid addition salt thereof.

A more preferred embodiment is the compound having the formula

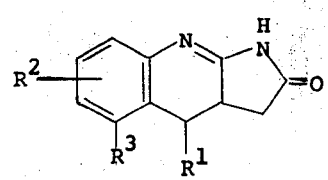

in which $R^1$ is H, phenyl or (lower)alkyl, $R^2$ and $R^3$ when different are hydrogen, chloro, bromo, fluoro, $CF_3$, $SO_3H$, hydroxy, nitro, amino, phenyl, (lower)alkyl or (lower)alkoxy of 1 to 3 carbon atoms, $R^2$ and $R^3$ when alike are hydrogen, chloro, bromo, fluoro, hydroxy, (lower)alkyl or (lower)alkoxy of 1 to 3 carbon atoms, or when taken together $R^2$ and $R^3$ are methylenedioxy or the residue of a phenyl ring (—CH=CH—CH=CH—); or a pharmaceutically acceptable acid addition salt thereof.

A more preferred embodiment is the compound having the formula

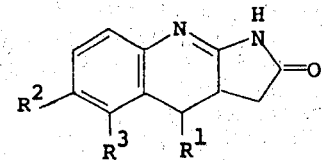

in which $R^1$ is H, phenyl or (lower)alkyl, $R^2$ and $R^3$ when different are hydrogen, chloro, bromo, fluoro, $CF_3$, $SO_3H$, hydroxy, nitro, amino, phenyl, (lower)alkyl or (lower)alkoxy of 1 to 3 carbon atoms, $R^2$ and $R^3$ when alike are hydrogen, chloro, bromo, fluoro, hydroxy, (lower)alkyl or (lower)alkoxy of 1 to 3 carbon atoms, or when taken together $R^2$ and $R^3$ are methylenedioxy or the residue of a phenyl ring (—CH=CH—CH=CH—); or a pharmaceutically acceptable acid addition salt thereof.

A still more preferred embodiment is the compound having the formula

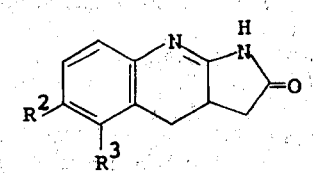

in which $R^2$ and $R^3$ when different are hydrogen, $CF_3$, $SO_3H$, chloro, bromo, fluoro, nitro, amino, hydroxy, (lower)alkyl or (lower)alkoxy of 1 to 3 carbon atoms, $R^2$ and $R^3$ when alike are hydrogen, chloro, bromo, fluoro, hydroxy, (lower)alkyl or (lower)alkoxy of 1 to 3 carbon atoms, or when taken together $R^2$ and $R^3$ are methylenedioxy or the residue of a phenyl ring (—CH=CH—CH=CH—); or a pharmaceutically acceptable acid addition salt thereof.

A most preferred embodiment is the compound having the formula

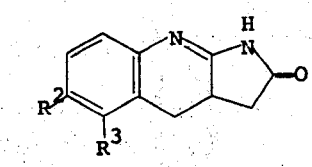

in which $R^2$ and $R^3$ when different are H, hydroxy, nitro, chloro, bromo, $CF_3$, fluoro, (lower)alkyl or (lower)alkoxy of 1 to 3 carbon atoms, $R^2$ and $R^3$ when alike are hydrogen, chloro, bromo, fluoro, hydroxy, (lower)alkyl or (lower)alkoxy of 1 to 3 carbon atoms; or a pharmaceutically acceptable salt thereof.

Another more preferred embodiment is the compound having the formula

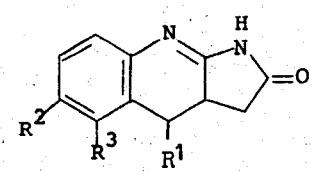

in which $R^2$ and $R^3$ are alike or different and are H, chloro, bromo, methoxy, methyl or hydroxy, and $R^1$ is H or (lower)alkyl; or the hydrochloride salt thereof.

The most preferred embodiments are the compounds of formula IM in which

1. $R^1$, $R^2$ are H;
2. $R^2$ and $R^3$ are chloro and $R^1$ is H;
3. $R^2$ is chloro, $R^3$ is methyl and $R^1$ is H;
4. $R^2$ is bromo, $R^3$ is methyl and $R^1$ is H;
5. $R^1$ and $R^2$ are H and $R^3$ is chloro;
6. $R^2$ is chloro, $R^3$ and $R^1$ are H;
7. $R^1$ and $R^2$ are H and $R^3$ is methyl;
8. $R^2$ is methyl and $R^3$ and $R^1$ is H;
9. $R^2$ and $R^3$ are methyl and $R^1$ is H;
10. $R^2$ and $R^3$ taken together are —CH=CH—CH=CH—; and $R^1$ is H;
11. $R^2$ is bromo, $R^3$ is chloro and $R^1$ is H;
12. $R^1$ is H, $R^2$ is $NO_2$ and $R^3$ is methyl; or the hydrochloride salts thereof;
13. $R^1$ and $R^2$ are H and $R^3$ is $CF_3$.
14. $R^1$ and $R^3$ are methyl.

For the purpose of this disclosure, the term (lower)alkyl shall mean straight and branched chain saturated aliphatic groups having 1 to 6 carbons inclusive. The term (lower)alkanol or (lower)alkoxy shall have the same connotation, an alcohol or alkoxy group of 1 to 6 carbons inclusive.

Pharmacological evaluation has indicated the compounds of the present invention possess hypotensive activity.

The blood pressure of unanesthetized rats and dogs was measured directly by means of a transducer attached to an intra-arterial cannula and in anesthetized dogs by a mercury manometer attached to a carotid cannula.

The compounds of the instant invention were tested as the hydrochloride salts by the above method in genetically hypertensive rats in doses of 50 mg./kg. orally.

At the present time, indications are that the compounds do not appear to be acting in the same way as 2-(2,6-dichloroanilino)-2-imidazoline hydrochloride [CATAPRES]. Their activity is probably not attributable to α-adrenergic blockade or to ganglionic blocking action.

In the treatment of hypertension in animals including man, the compounds of the present invention are administered orally and/or parenterally, in accordance with conventional procedures for the administration of hypotensive agents in an amount of from about 0.5 mg.kg./dose to 30 mg./kg./dose depending upon the route of administration and the particular compound of the invention. The preferred dosage for the compounds of the invention is in the range of about 1.0 to 15.0 mg./kg./dose two to four times a day.

Pharmacological evaluation has also indicated the compounds of the present invention possess blood platelet anti-aggregative activity.

The aggregometer method of Born (1), as modified by Mustard et al (2) was used to assess the in vitro activity of the various compounds as to inhibition of adenosine diphosphate (ADP) and collagen induced platelet aggregation. Platelet rich plasma was separated by centrifugation from citrated (3.8 per cent) rabbit blood. ADP in final concentration of 0.5 mcg./ml. or 0.05 ml. of a collagen suspension prepared according to the method described by Evans et al. (3) was used to induce aggregation. The various compounds tested were dissolved in dimethylsulfoxide (DMSO) so that 5 mcl. added to the platelet rich plasma would yield the desired test concentration. Vehicle control trials were done and compared with aggregation induced in platelet rich plasma containing various concentrations of the test compounds. Dose response curves were obtained and Effective Concentration (EC50) values calculated.

1. Born, G.V.R J. Physiol., London, 162, 67P (1962).
2. Mustard, J. F., Hegardt, B. Rowsell, H. C. and MacMillan, R. L., J. Lab. Clin. Med. 64, 548 (1964).
3. Evans, G. Marian, M. C., Packham, M. A., Nishizawa, E. E., Mustard, J. F. and Murphy, E. A., J. Exp. Med., 128, 877 (1968).

Table I is illustrative of the hypotensive activity of some of the preferred embodiments of the present invention.

Antihypertensive Activity

Compounds were studied by oral administration in conscious rats for their effects on aortic pressure and cardiac rate. BL-4412, resulted in an appreciable fall in aortic pressure. The increase in heart rate in this study was not out of proportion to the fall in aortic pressure.

TABLE I

Effect of Compounds on mean aortic pressure and heart rate in conscious rats.

| Compound | Dose mg/kg po | Time Min | Aortic Pressure mmHg | Aortic Pressure % Change | Heart Rate Beats/Min | % Change |
|---|---|---|---|---|---|---|
| BL-4369 | 50 (N=3) | 0 | 114±2 | — | 350±25 | — |
| | | 30 | 91±6 | −20±6 | 420±19 | 21±9 |
| | | 90 | 110±3 | −3±4 | 414±26 | 19±9 |
| | | 150 | 101±3 | −11±2 | 370±31 | 6±8 |
| | | 300 | 109±8 | −4±7 | 382±25 | 10±7 |
| BL-4412 | 50 (N=3) | 0 | 126±2 | — | 352±21 | — |
| | | 30 | 86±1 | −32 | 464±24 | 34±15 |
| | | 90 | 86±2 | −31.2 | 432±12 | 24±10 |
| | | 150 | 89±4 | −29 | 422±12 | 21±11 |
| | | 300 | 95±4 | −25 | 422±19 | 21±12 |

+Denotes an increase in b.p.
−Denotes a decrease in b.p.

Table II is illustrative of the blood platelet anti-aggregative activity of some of the preferred embodiments of the present invention.

TABLE II

| | $EC_{50}$(ug/ml) (In Vitro) | |
|---|---|---|
| | ADP | Collagen |
| BL-4369 | 22 | 27 |
| BL-4412 | 1.5 | 0.3 |

EXPERIMENTAL

All products described are supported by satisfactory infrared (IR) and nuclear magnetic resonance (nmr) spectra. Melting points are uncorrected. Temperatures are expressed in degrees Centigrade (°C.) and pressures in millimeters of mercury (mm).

EXAMPLE 1

Ethyl 3,3-dicarbethoxy-4-(2-nitrophenyl)butyrate, $\underline{1}^a$ ($R^2 = R^3 = H$).

A 500 ml. Morton flask equipped with a condenser, stirrer, and dropping funnel was flame dried and charged with NaH (11.9 g - 61% dispersion in mineral oil; 0.3 mole) and 150 ml. of 10% DMF in benzene. Triethyl 1,1,2-ethanetricarboxylate (73.9 g; 0.3 mole) was then added with vigorous stirring over a one hour period. After stirring at room temperature for 0.5 hour, there was then added as rapidly as possible o-nitrobenzyl chloride (51.5 g; 0.3 mole). The resulting reaction mixture was heated at reflux for 23 hours. After cooling, insoluble material was removed by filtration (supercel). Water was added to the filtrate followed by aqueous HCl to acidify the aqueous layer. Extraction with ether followed. The combined ethereal extracts were then washed twice with water, once with brine, dried over $Na_2SO_4$, filtered and rendered free of solvent in vacuo. The viscous oil so obtained was dissolved in acetonitrile and washed with n-pentane to remove the mineral oil. Removal of the acetonitrile afforded the crude product. The IR (infrared) and NMR (nuclear magnetic resonance) spectra were consistent with the structure and this material was used directly in the next step without further purification.

EXAMPLE 2

3-Carboxy-4-(2-nitrophenyl)butyric acid, $\underline{2}^a$ ($R^2 = R^3 = H$).

A mixture of $\underline{1}^a$ ($R^2 = R^3 = H$) (114 g; 0.3 mole) and 400 ml. 48% HBr was heated at reflux with an oil bath at 140° C for 18 hours. After this time, the reaction mixture was concentrated to near dryness. The solids were filtered, washed with cold water and dried under high vacuum at 60° C. The crude product was dissolved in 150 ml. 5N NaOH. The insolubles were removed by filtration and the solution was washed with ether. After acidifying and concentrating the aqueous solution, the product was filtered, washed with cold water and dried. This material was recrystallized from ethyl acetateSkellysolve B (essentially n-hexane) with decolorization by charcoal. A white, crystalline material was obtained, m.p. 135°–138° C (40.4 g; 53.4%). A further recrystallization gave the analytical sample, m.p. 137°–138° C. The IR and NMR were consistent with the structure.

Calculated for $C_{11}H_{11}NO_6$: C, 52.17%; H, 4.38%; N, 5.53%; Found: C, 51.69%; H, 4.54%; N, 5.21%

EXAMPLE 3

1,2,3,4-Tetrahydroquinoline-2-one-3-acetic acid, $\underline{3}^a$ ($R^2 = R^3 = H$).

A mixture of $\underline{2}^a$ ($R^2 = R^3 = H$) (14.8 g; 0.059 mole) and 1.0 g. of 10% Pd on carbon in 300 ml. of absolute ethanol was shaken under 50 lbs. of hydrogen on a Parr apparatus. The exothermic reaction was kept at 30°C by water cooling. After uptake was complete, the catalyst was filtered and was washed with 30 ml. hot DMF. The filtrate was concentrated to 200 ml. and refluxed for one hour. Concentration to 50 ml. and addition of water afforded a solid precipitate which was collected, washed with cold water and dried. There was obtained 10.95 g. (91%) of pure product, m.p. 199°–210°C. A sample recrystallized from ethanolSkellysolve B gave m.p. 199°–201°C.

Calculated for $C_{11}H_{11}NO_3$: C, 64.38%; H, 5.40%; N, 6.83%; Found: C, 64.35%; H, 5.69%; N, 6.53%

EXAMPLE 4

Methyl 1,2,3,4-tetrahydroquinoline-2-one-3-acetate, $\underline{4}^a$ ($R^2 = R^3 = H$).

A mixture of $\underline{3}^a$ ($R^2 = R^3 = H$) (15.3 g; 0.075 mole) and 6 ml. conc. $H_2SO_4$ in 250 ml. of $CH_3OH$ was refluxed for 6 hours. After evaporation to dryness, water was added and the crystalline solids filtered and dried. There was obtained 15.7 g. (95.8%) of product, m.p. 146°–147°C. Recrystallization from ethyl acetate-Skellysolve B gave the analytical sample, m.p. 147°–148°C. The IR and NMR were consistent with the structure.

Calculated for $C_{12}H_{13}NO_3$: C, 65.74%; H, 5.98%; N, 6.39%; Found: C, 65.83%; H, 6.25%; N, 6.12%

EXAMPLE 5

1-H-2,3,3a,4-Tetrahydro-2-oxopyrrolo[2,3-b]quinoline, $\underline{6}^a$ ($R^2 = R^3 = H$).

A mixture of $\underline{4}^a$ ($R^2 = R^3 = H$) (3.1g; 0.015 mole) and triethyloxonium tetrafluoroborate (5.1 g; 0.027 mole) in 50 ml. dry $CH_2Cl_2$ was stirred at room temperature for 3 hours. After cooling, $K_2CO_3$ (2.23 g; 0.016 mole) was added together with 2.2 ml. water. The resulting mixture was stirred at room temperature for 15 minutes. Sodium sulfate was added and again the mixture was stirred for 10 minutes. After filtration and evaporation of the solvent, the intermediate $\underline{5}^a$ ($R^2 = R^3 = H$) was obtained as a viscous oil. This oil was dissolved in 100 ml. of ethanol saturated with ammonia and allowed to stand at room temperature for 3 hours after which time the solution was heated at reflux for 17 hours. After cooling, the separated solids were collected, washed with cold ethanol and dried. In this way, there was obtained 3.36 g. of material which was a mixture of product and fluoroborate containing complexes. This material was dissolved in 5% HCl, and filtered from insolubles. The filtrate was made basic with conc. $NH_4OH$, thereby affording as a solid 2.3 g. (55.9%) of pure product m.p. 285°–290°C after collecting and drying. A sample recrystallized from dimethylformamide-$H_2O$ gave the analytically pure material m.p.

297°–299°C. The IR and NMR were consistent with the structure.

Calculated for $C_{11}H_{10}N_2O$: C, 70.95%; H, 5.41%; N, 15.05%; Found: C, 70.87%; H, 5.62%; N, 15.35%

EXAMPLE 6

Ethyl 3,3-dicarbethoxy-4-(2-nitro-6-methylphenyl)butyrate, $\underline{1}^b$ ($R^2 = H$; $R^3 = CH_3$).

The title compound was prepared by the same procedure as described in example 1 for $\underline{1}^a$ ($R^2 = R^3 = H$), using triethyl 1,1,2-ethanetricarboxylate (9.85 g; 0.04 mole), NaH (1.6 g; 0.04 mole) and 2-nitro-6-methylbenzyl chloride (7.4 g; 0.04 mole) in 20 ml. 10% dimethylformamide (DMF) in benzene. The crude product so obtained was used directly in the next step without further purification.

EXAMPLE 7

3-Carboxy-4-(2-nitro-6-methylphenyl)butyric acid, $\underline{2}^b$ ($R^2 = H$; $R^3 = CH_3$).

The title compound was prepared by the same procedure as described in example 2 for $\underline{2}^a$ ($R^2 = R^3 = H$), except that $\underline{1}^b$ ($R^2 = H$; $R^3 = CH$) was used as the starting material. A yield of 60.8% was realized; m.p. 172°–176°C. Recrystallization from ethyl acetate-Skellysolve B afforded the analytical sample; m.p. 178°–180°C.

Calculated for $C_{12}H_{13}NO_6$: C, 53.93%; H, 4.90%; N, 5.24%; Found: C, 53.95%; H, 5.15%; N, 5.33%

EXAMPLE 8

1,2,3,4-Tetrahydro-5-methylquinoline-2-one-3-acetic, $\underline{3}^b$ ($R^2 = H$; $R^3 = CH_3$).

The title compound was prepared by the same procedure as described for $\underline{3}^a$ in example 3 ($R^2 = R^3 = H$), except that $\underline{2}^b$ ($R^2 = H$; $R^3 = CH_3$) was used as the starting material. An 85% yield of product was realized; m.p. 234° – 237°C. A sample recrystallized from hot DMF-water; m.p. 239°–241°C.

Calculated for $C_{12}H_{13}NO_3$: C, 65.74%; H, 5.98%; N, 6.39%; Found: C, 65.47%; H, 6.17%; N, 6.34%

EXAMPLE 9

Methyl 1,2,3,4-tetrahydro-5-methylquinoline-2-one-3-acetate, $\underline{4}^b$ ($R^2 = H$; $R^3 = CH_3$).

The title compound was prepared by the same procedure as described for $\underline{4}^a$ ($R^2 = R^3 = H$) except that $\underline{3}^b$ ($R^2 = H$, $R^3 = CH_3$) was used as the starting material. There was obtained after recrystallization of the crude product from methanol-water a 72.2% yield of pure product; m.p. 134°–135°C.

Calculated for $C_{13}H_{15}NO_3$: C, 66.93%; H, 6.48%; N, 6.01%; Found: C, 67.21%; H, 6.60%; N, 5.84%

EXAMPLE 10

1-H-2,3,3a,4-Tetrahydro-5-methyl-2-oxopyrrolo[2,3-b]-quinoline, $\underline{6}^b$ ($R^2 = H$; $R^3 = CH_3$).

The title compound was prepared by the same procedure as described for $\underline{6}^b$ ($R^2 = R^3 = H$) except that $\underline{4}^b$ ($R^2 = H$; $R^3 = CH_3$) was used as the starting material. A 59.6% yield of pure product was obtained; m.p. 282°–287°C. Recrystallization for DMF-water afforded the analytical sample; m.p. 282°–290°C.

Calculated for $C_{12}H_{12}N_2O$: C, 71.97%; H, 6.04%; N, 13.99%; Found: C, 71.87%; H, 6.27%; N, 13.71%

EXAMPLE 11

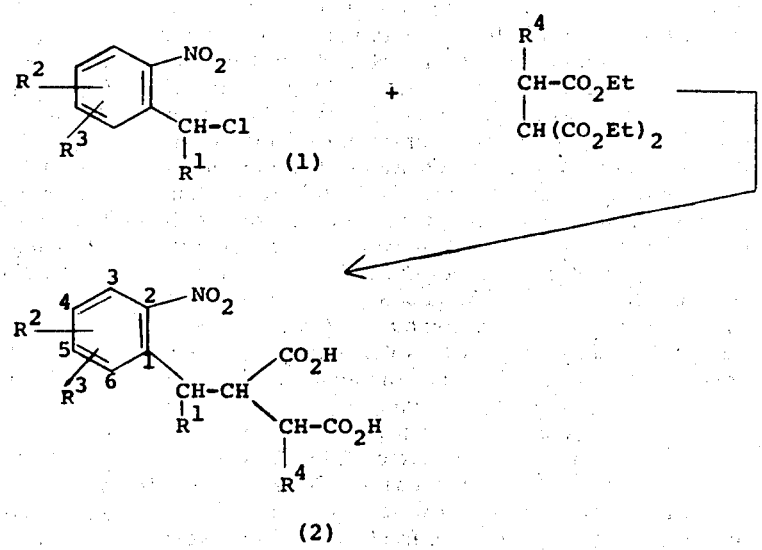

Preparation of Substituted 3-Carboxy-4-(2-nitrophenyl) butyric acids following the procedure of Examples 1 and 2

Consecutive substitution in the procedures of examples 1 and 2 for the o-nitrobenzyl chloride and triethyl 1,1,2-ethanetricarboxylate used therein of equimolar quantities of the appropriately $R^1$, $R^2$, $R^3$ and $R^4$ substituted o-nitrobenzyl chloride and triethyl 1,1,2-ethanetricarboxylate produces the compounds having formula 2 in which $R^1$, $R^2$, $R^3$ and $R^4$ are as designated:

| Compound No. | $R^1$ | $R^2$ | $R^3$ | $R^4$ |
|---|---|---|---|---|
| 2C | H | H | 6-Cl | H |
| 2D | H | H | 5-Cl | H |

-continued

| Compound No. | R¹ | R² | R³ | R⁴ |
|---|---|---|---|---|
| 2E | H | H | 4-Cl | H |
| 2F | H | H | 3-Cl | H |
| 2G | H | H | 4-F | H |
| 2H | H | H | 6-CH₃ | H |
| 2I | H | H | 5-CH₃ | H |
| 2J | H | H | 3-CH₃ | H |
| 2K | H | H | 6-OCH₃ | H |
| 2L | H | H | 5-OCH₃ | H |
| 2M | H | H | 3-OCH₃ | H |
| 2N | H | 5-OCH₃ | 6-OCH₃ | H |
| 2O | H | 4-OCH₃ | 5-OCH₃ | H |
| 2P | H | R² and R³ are methylenedioxy | | H |
| 2Q | H | H | H | CH₃ |
| 2R | H | H | 6-Cl | CH₃ |
| 2S | H | H | 6-CH₃ | CH₃ |
| 2T | H | H | 5-CH₃ | CH₃ |
| 2U | H | H | 3-CH₃ | CH₃ |
| 2V | H | H | 6-OCH₃ | CH₃ |
| 2W | H | H | 5-OCH₃ | CH₃ |
| 2X | H | H | 3-OCH₃ | CH₃ |
| 2Y | H | 4-OCH₃ | 5-OCH₃ | CH₃ |
| 2Z | CH₃ | H | H | H |
| 2AA | CH₃ | H | H | H |
| 2BB | H | 3-CH₃ | 6-CH₃ | H |
| 2CC | H | H | 6-Br | H |
| 2DD | H | H | 6-F | H |
| 2EE | H | H | H | C₂H₅ |
| 2FF | H | H | CH₃ | CH₃ |
| 2GG | H | H | CF₃ | H |
| 2HH | C₆H₅ | H | H | H |
| 2II | H | 5-CH₃ | 6-CH₃ | H |
| 2JJ | H | 5-Cl | 6-Cl | H |
| 2KK | C₆H₅ | H | 6-Br | H |
| 2LL | CH₃ | H | 6-CH₃ | H |

-continued

| Compound No. | R¹ | R² | R³ | R⁴ |
|---|---|---|---|---|
| 3G | H | H | 7-F | H |
| 3H | H | H | 5-CH₃ | H |
| 3I | H | H | 6-CH₃ | H |
| 3J | H | H | 8-CH₃ | H |
| 3K | H | H | 5-OCH₃ | H |
| 3L | H | H | 6-OCH₃ | H |
| 3M | H | H | 8-OCH₃ | H |
| 3N | H | 6-OCH₃ | 5-OCH₃ | H |
| 3O | H | 7-OCH₃ | 6-OCH₃ | H |
| 3P | H | R² and R³ are methylenedioxy | | H |
| 3Q | H | H | H | CH₃ |
| 3R | H | H | 5-Cl | CH₃ |
| 3S | H | H | 5-CH₃ | CH₃ |
| 3T | H | H | 6-CH₃ | CH₃ |
| 3U | H | H | 8-CH₃ | CH₃ |
| 3V | H | H | 5-OCH₃ | CH₃ |
| 3W | H | H | 6-OCH₃ | CH₃ |
| 3X | H | H | 8-OCH₃ | CH₃ |
| 3Y | H | 7-OCH₃ | 6-OCH₃ | CH₃ |
| 3Z | CH₃ | H | H | H |
| 3AA | CH₃ | H | H | H |
| 3BB | H | 8-CH₃ | 5-CH₃ | H |
| 3CC | H | H | 5-Br | H |
| 3DD | H | H | 5-F | H |
| 3EE | H | H | H | C₂H₅ |
| 3FF | H | H | 5-CH₃ | CH₃ |
| 3HH | C₆H₅ | H | H | H |
| 3II | H | 6-CH₃ | 5-CH₃ | H |
| 3JJ | H | 6-Cl | 5-Cl | H |
| 3KK | C₆H₅ | 5-Br | H | H |
| 3LL | CH₃ | H | 5-CH₃ | H |

EXAMPLE 12

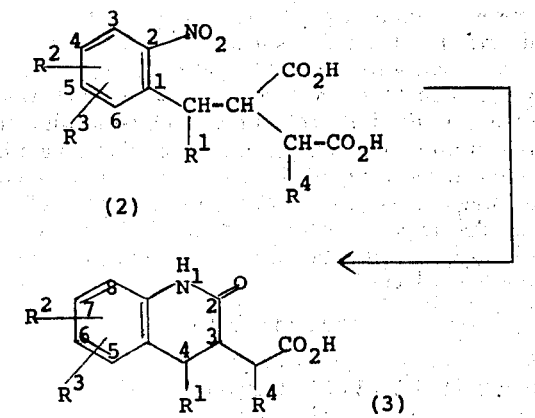

Preparation of Substituted 1,2,3,4-Tetrahydroquinoline-2-one-3-acetic acid via example 3

Substitution in the procedure of example 3 for the 3-carboxy-4-(2-nitrophenyl)butyric acid used therein of an equimolar quantity of an appropriately substituted 3-carboxy-4-(2-nitrophenyl)butyric acid produces the compounds having formula 3 in which R¹, R², R³ and R⁴ are as designated:

| Compound No. | R¹ | R² | R³ | R⁴ |
|---|---|---|---|---|
| 3C | H | H | 5-Cl | H |
| 3D | H | H | 6-Cl | H |
| 3E | H | H | 7-Cl | H |
| 3F | H | H | 8-Cl | H |

EXAMPLE 13

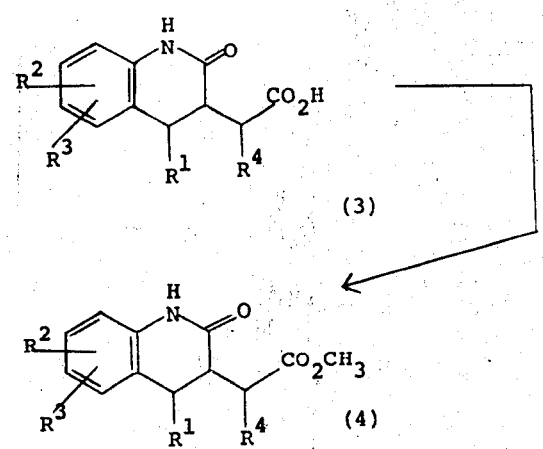

Preparation of Substituted Methyl 1,2,3,4-Tetrahydroquinoline-2-one-3-acetates via example 4

Substitution in the procedure of example 3 for the 1,2,3,4-tetrahydroquinoline-2-one-3-acetic acid used therein of an equimolar quantity of an appropriately substituted 1,2,3,4-tetrahydroquinoline-2-one-3-acetic acid produces the compounds having the formula 4 in which R¹, R², R³ and R⁴ are as designated:

| Compound No. | R¹ | R² | R³ | R⁴ |
|---|---|---|---|---|
| 4C | H | H | 5-Cl | H |
| 4D | H | H | 6-Cl | H |
| 4E | H | H | 7-Cl | H |
| 4F | H | H | 8-Cl | H |
| 4G | H | H | 7-F | H |
| 4H | H | H | 5-CH₃ | H |

-continued

| Compound No. | R¹ | R² | R³ | R⁴ |
|---|---|---|---|---|
| 4I | H | H | 6-CH₃ | H |
| 4J | H | H | 8-CH₃ | H |
| 4K | H | H | 5-OCH₃ | H |
| 4L | H | H | 6-OCH₃ | H |
| 4M | H | H | 8-OCH₃ | H |
| 4N | H | 6-OCH₃ | 5-OCH₃ | H |
| 4O | H | 7-OCH₃ | 6-OCH₃ | H |
| 4P | H | R² and R³ are methylenedioxy | | H |
| 4Q | H | H | H | CH₃ |
| 4R | H | H | 5-Cl | CH₃ |
| 4S | H | H | 5-CH₃ | CH₃ |
| 4T | H | H | 6-CH₃ | CH₃ |
| 4U | H | H | 8-CH₃ | CH₃ |
| 4V | H | H | 5-OCH₃ | CH₃ |
| 4W | H | H | 6-OCH₃ | CH₃ |
| 4X | H | H | 8-OCH₃ | CH₃ |
| 4Y | H | 7-OCH₃ | 6-OCH₃ | CH₃ |
| 4Z | CH₃ | H | H | H |
| 4AA | CH₃ | H | H | H |
| 4BB | H | 8-CH₃ | 5-CH₃ | H |
| 4CC | H | H | 5-Br | H |
| 4DD | H | H | 5-F | H |
| 4EE | H | H | H | C₂H₅ |
| 4FF | H | H | 5-CH₃ | CH₃ |
| 4HH | C₆H₅ | H | H | H |
| 4II | H | 6-CH₃ | 5-CH₃ | H |
| 4JJ | H | 6-Cl | 5-Cl | H |
| 4KK | C₆H₅ | H | 5-Br | H |
| 4LL | CH₃ | H | 5-CH₃ | H |

EXAMPLE 14

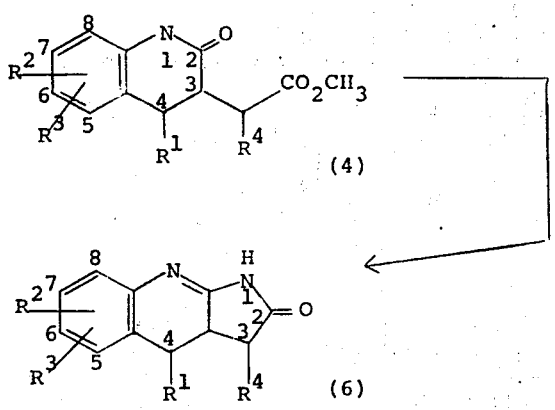

Preparation of Substituted
1-H-2,3,3a,4-Tetrahydro-2-oxo-pyrrolo[2,3-b]quinolines via example 5

Substitution in the procedure of example 5 for the methyl 1,2,3,4-tetrahydroquinoline-2-one-3-acetic acid used therein of an equimolar quantity of an appropriately substituted 1,2,3,4-tetrahydroquinoline-2-one-3-acetic acid produces the compounds having formula 6 in which R¹, R², R³ and R⁴ are as designated:

| Compound No. | R¹ | R² | R³ | R⁴ |
|---|---|---|---|---|
| 6C | H | H | 5-Cl | H |
| 6D | H | H | 6-Cl | H |
| 6E | H | H | 7-Cl | H |
| 6F | H | H | 8-Cl | H |
| 6G | H | H | 7-F | H |
| 6H | H | H | 5-CH₃ | H |
| 6I | H | H | 6-CH₃ | H |
| 6J | H | H | 8-CH₃ | H |
| 6K | H | H | 5-OCH₃ | H |

-continued

| Compound No. | R¹ | R² | R³ | R⁴ |
|---|---|---|---|---|
| 6L | H | H | 6-OCH₃ | H |
| 6M | H | H | 8-OCH₃ | H |
| 6N | H | 6-OCH₃ | 5-OCH₃ | H |
| 6O | H | 7-OCH₃ | 6-OCH₃ | H |
| 6P | H | R² and R³ are methylenedioxy | | H |
| 6Q | H | H | H | CH₃ |
| 6R | H | H | 5-Cl | CH₃ |
| 6S | H | H | 5-CH₃ | CH₃ |
| 6T | H | H | 6-CH₃ | CH₃ |
| 6U | H | H | 8-CH₃ | CH₃ |
| 6V | H | H | 5-OCH₃ | CH₃ |
| 6W | H | H | 6-OCH₃ | CH₃ |
| 6X | H | H | 8-OCH₃ | CH₃ |
| 6Y | H | 7-OCH₃ | 6-OCH₃ | CH₃ |
| 6Z | CH₃ | H | H | H |
| 6AA | CH₃ | H | H | H |
| 6BB | H | 8-CH₃ | 5-CH₃ | H |
| 6CC | H | H | 5-Br | H |
| 6DD | H | H | 5-F | H |
| 6EE | H | H | H | C₂H₅ |
| 6FF | H | H | 5-CH₃ | CH₃ |
| 6HH | C₆H₅ | H | H | H |
| 6II | H | 6-CH₃ | 5-CH₃ | H |
| 6JJ | H | 6-Cl | 5-Cl | H |
| 6KK | C₆H₅ | 5-Br | H | H |
| 6LL | CH₃ | H | 5-CH₃ | H |

EXAMPLE 15

Preparation of 6-chloro-5-methyl-1-H-2,3,3a,4-Tetrahydro-2-oxo-pyrrolo[2,3-b]quinolines.

To a vigorously stirred solution of 0.01 mole of 5-methyl-1-H-2,3,3a,4-tetrahydro-2-oxo-pyrrolo[2,3-b]quinoline in 40 ml. of glacial acetic acid is added dropwise at room temperature 1.60 g. (0.01 mole) of chlorine. The mixture is stirred at room temperature for one hour, water (50 ml.) is added and the volume concentrated (10-15ml.) in vacuo. Additional water (50 ml.) is added, the solution is made basic with ammonium hydroxide, warmed and the insoluble material filtered under suction. The colorless solid is washed with water, dried and crystallized from 50 ml. of 5% hydrochloric acid yielding crude solid. Purification is effected by crystallization from methanol/ether to yield the title product.

EXAMPLE 16

Preparation of 6-Nitro-1-H-2,3,3a,4-Tetrahydro-2-oxopyrrolo[2,3-b]quinoline.

1-H-2,3,3a,4-tetrahydro-2-oxo-pyrrolo[2,3-b]-quinoline (0.06 moles) in 150 ml of tetrahydrofuran, chilled to 0°C, is added dropwise to a stirred solution of 5% nitric acid in sulfuric acid (83.0 g; 6.6 × 10⁻¹² moles of nitric acid). The mixture is allowed to stir at 0° for 45 minutes, warmed to room temperature and stirred an additional two hours. The mixture is poured into 700 ml. of ice water, the organic layer separated, the acidic aqueous solution washed with methylene chloride (2 × 100 ml.) and filtered. The aqueous solution is made basic (pH 8) by the dropwise addition of 40% sodium hydroxide, the basic solution is stirred for 30 minutes and the precipitate filtered under suction. The yellow solid is washed with water, then acetone and dried under high vacuum. The solid is suspended in water (350 ml.), the solution saturated with hydrogen chloride, heated to boiling and filtered. Saturated sodium chloride solution (100 ml.) is added, the mixture cooled and the precipitate isolated to yield the desired product.

EXAMPLE 17

Preparation of 6-Bromo-5-methyl-1-H-2,3,3a,4-Tetrahydro-2-oxo-pyrrolo[2,3-b]quinoline.

To a solution of 1.30 g (8 mmole) of anhydrous ferric chloride in 30 ml of nitromethane is added 5 mmoles of solid 5-methyl-1-H-2,3,3a,4-tetrahydro-2-oxo-pyrrolo[2,3-b]quinoline and 0.80 g (5 mmole) of bromine. The system is stoppered, warmed to 50° in an oil bath overnight, cooled to room temperature and the solvent removed in vacuo. The resulting solid is suspended in water (50 ml), the mixture made basic (pH 10) with sodium bicarbonate and stirred at room temperature for 20 mins. The solid is filtered under suction, washed with water, then isopropyl alcohol and dried to yield a powder. Purification is effected by formation of the hydrochloride salt from acetonitrile.

EXAMPLE 18

Preparation of 6-Amino-1-H-2,3-3a,4-Tetrahydro-2-oxopyrrolo[2,3-b]quinoline

To a suspension of 0.1 mole of 6-nitro-1-H-2,3,3a,4-tetrahydro-2-oxopyrrolo[2,3-b]quinoline in 95% ethanol (300 ml.) is added 10 ml. of concentrated hydrochloric acid and 0.45 g. of 10% Pd/C catalyst. The mixture is placed on a Paar hydrogenator, shaken until theoretical hydrogen absorbed, removed and water (150 ml.) added to effect dissolution of the precipitate. The mixture is filtered under suction, the catalyst washed with 95% ethanol and the mixture evaporated to dryness yielding the desired title product.

We claim:

1. A compound having the formula

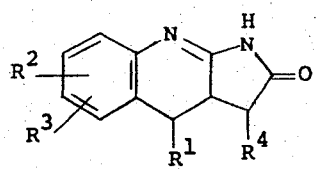

in which $R^1$ and $R^4$ are alike or different and each is H, phenyl or (lower)alkyl of 1 to 3 carbon atoms, $R^2$ and $R^3$ when different are hydrogen, chloro, bromo, fluoro, $CF_3$, hydroxy, nitro, amino, phenyl, (lower)alkyl of 1 to 3 carbon atoms, or (lower)alkoxy of 1 to 3 carbon atoms, $R^2$ and $R^3$ when alike are hydrogen, chloro, fluoro, bromo, hydroxy, (lower)alkyl of 1 to 3 carbon atoms, or (lower)alkoxy of 1 to 3 carbon atoms or when taken together $R^2$ and $R^3$ are methylenedioxy or the residue of a phenyl ring (—C=CH—CH=CH—); or a pharmaceutically acceptable salt thereof.

2. A compound of claim 1 having the formula

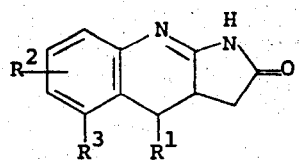

in which $R^1$ is H, phenyl or (lower)alkyl of 1 to 3 carbon atoms, $R^2$ and $R^3$ when different are hydrogen, chloro, bromo, fluoro, $CF_3$, hydroxy, nitro, amino, phenyl, (lower)alkyl of 1 to 3 carbon atoms, or (lower)alkoxy of 1 to 3 carbon atoms, $R^2$ and $R^3$ when alike are hydrogen, chloro, bromo, fluoro, hydroxy, (lower)alkyl of 1 to 3 carbon atoms, or (lower)alkoxy of 1 to 3 carbon atoms, or when taken together $R^2$ and $R^3$ are methylenedioxy or the residue of a phenyl ring (—CH=CH—CH=CH—); or a pharmaceutically acceptable acid addition salt thereof.

3. A compound of claim 1 having the formula

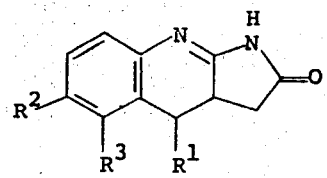

in which $R^1$ is H, phenyl or (lower)alkyl of 1 to 3 carbon atoms, $R^2$ and $R^3$ when different are hydrogen, chloro, bromo, fluoro, $CF_3$, hydroxy, nitro, amino, phenyl, (lower)alkyl of 1 to 3 carbon atoms, or (lower)alkoxy of 1 to 3 carbon atoms, $R^2$ and $R^3$ when alike are hydrogen, chloro, bromo, fluoro, hydroxy, (lower)alkyl of 1 to 3 carbon atoms, or (lower)alkoxy of 1 to 3 carbon atoms, or when taken together $R^2$ and $R^3$ are methylenedioxy or the residue of a phenyl ring (—CH=CH—CH=CH—); or a pharmaceutically acceptable acid addition salt thereof.

4. A compound of claim 1 having the formula

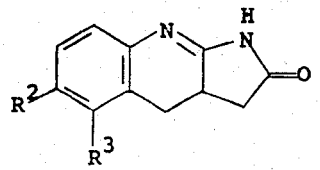

in which $R^2$ and $R^3$ when different are hydrogen, $CF_3$, chloro, bromo, fluoro, nitro, amino, hydroxy, (lower)alkoxy of 1 to 3 carbon atoms, or (lower)alkyl of 1 to 3 carbon atoms, $R^2$ and $R^3$ when alike are hydrogen, chloro, bromo, fluoro, hydroxy, (lower)alkyl of 1 to 3 carbon atoms, or (lower)alkoxy of 1 to 3 carbon atoms, or when taken together $R^2$ and $R^3$ are methylenedioxy or the residue of a phenyl ring (—CH=CH—CH=CH—); or a pharmaceutically acceptable acid addition salt thereof.

5. A compound of claim 1 having the formula

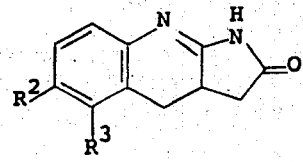

in which $R^2$ and $R^3$ are alike or different and are H, hydroxy, bromo, chloro, fluoro (lower)alkyl of 1 to 3 carbon atoms, or (lower)alkoxy of 1 to 3 carbon atoms; or a pharmaceutically acceptable salt thereof.

6. A compound of claim 1 having the formula

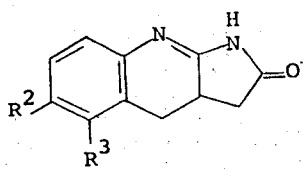

in which $R^2$ and $R^3$ are alike or different and are H, chloro, bromo, methyl, methoxy, or hydroxy; or the hydrochloride salt thereof.

7. The compound of claim 6 in which $R^2$ and $R^3$ are H.

8. The compound of claim 6 in which $R^2$ and $R^3$ are chloro

9. The compound of claim 6 in which $R^2$ is chloro and $R^3$ is methyl.

10. The compound of claim 6 in which $R^2$ is bromo and $R^3$ is methyl.

11. The compound of claim 6 in which $R^2$ is H and $R^3$ is chloro.

12. The compound of claim 6 in which $R^2$ is chloro and $R^3$ is H;

13. The compound of claim 6 in which $R^2$ is H and $R^3$ is methyl;

14. The compound of claim 6 in which $R^2$ is methyl and $R^3$ is H;

15. The compound of claim 6 in which $R^2$ and $R^3$ are methyl;

16. The compound of claim 4 in which $R^2$ and $R^3$ taken together are $-CH=CH-CH=CH-$;

17. The compound of claim 6 in which $R^2$ is bromo and $R^3$ is chloro.

18. The compound of claim 4 in which $R^2$ is $NO_2$ and $R^3$ is methyl.

19. The compound of claim 3 in which $R^1$ and $R^3$ are methyl and $R^2$ is H.

* * * * *